(12) United States Patent
Westerlund

(10) Patent No.: US 9,333,228 B2
(45) Date of Patent: May 10, 2016

(54) NUTRITIONAL SUPPLEMENT FOR RECOVERY, REPAIR, AND MAINTENANCE

(75) Inventor: Erik Westerlund, Columbus, GA (US)

(73) Assignee: Top Doctors Labs, LLC, Gainesville, FL (US)

( * ) Notice: Subject to any disclaimer, the term of this patent is extended or adjusted under 35 U.S.C. 154(b) by 1380 days.

(21) Appl. No.: 13/149,614

(22) Filed: May 31, 2011

(65) Prior Publication Data

US 2011/0293759 A1    Dec. 1, 2011

Related U.S. Application Data

(60) Provisional application No. 61/350,293, filed on Jun. 1, 2010.

(51) Int. Cl.

| | | |
|---|---|---|
| *A61K 8/67* | (2006.01) |
| *A61K 36/185* | (2006.01) |
| *A61K 31/122* | (2006.01) |
| *A61K 31/194* | (2006.01) |
| *A61K 31/593* | (2006.01) |
| *A61K 33/06* | (2006.01) |
| *A61K 33/34* | (2006.01) |
| *A61K 38/19* | (2006.01) |

(52) U.S. Cl.
CPC ............ *A61K 36/185* (2013.01); *A61K 31/122* (2013.01); *A61K 31/194* (2013.01); *A61K 31/593* (2013.01); *A61K 33/06* (2013.01); *A61K 33/34* (2013.01); *A61K 38/195* (2013.01)

(58) Field of Classification Search
CPC ........................................................ A61K 8/67
See application file for complete search history.

(56) References Cited

U.S. PATENT DOCUMENTS

| 4,491,347 A * | 1/1985 | Gustafson ................. 285/47 |
| 2004/0258801 A1* | 12/2004 | Ling et al. ............... 426/72 |
| 2006/0115556 A1* | 6/2006 | Foulger et al. ........... 426/72 |
| 2006/0134244 A1* | 6/2006 | Takemoto ............... 424/766 |
| 2006/0166948 A1* | 7/2006 | Vermeer ................. 514/167 |
| 2008/0118603 A1* | 5/2008 | Lada et al. ............. 426/66 |
| 2009/0061023 A1* | 3/2009 | Albritton, IV .......... 424/639 |

FOREIGN PATENT DOCUMENTS

JP    54076598 A  *  6/1979

OTHER PUBLICATIONS

Rightway Vitamins Online; URL < http://www.rightwayvitamins.net/page36.php>, May 12, 2006, 7 pages.*

* cited by examiner

*Primary Examiner* — Patricia A Leith
(74) *Attorney, Agent, or Firm* — DLA Piper LLP (US)

(57) ABSTRACT

The present invention provides dietary supplement formulations that may be beneficial for developing and strengthening bones and joints. Also provided are methods of treating a bone disease, such as osteoporosis, and methods of strengthening bones and joints by administering the dietary supplements to a subject in need thereof.

3 Claims, No Drawings

NUTRITIONAL SUPPLEMENT FOR RECOVERY, REPAIR, AND MAINTENANCE

CROSS-REFERENCE TO RELATED APPLICATION

This application claims the benefit of priority under 35 U.S.C. §119(e) to U.S. Provisional Application No. 61/350,293 filed Jun. 1, 2010, the disclosure of which is hereby incorporated by reference in its entirety for all purposes.

BACKGROUND OF THE INVENTION

1. Field of the Invention

The invention relates generally to a composition of a dietary supplement for developing and strengthening bones and joints.

2. Background Information

Bone can be an extremely metabolically active and dynamic tissue. This is especially true after bone or joint surgery (such total knee replacement, total hip replacement, shoulder surgery, knee ACL surgery and others). Healing or fractured bones have unique nutritional and physiologic requirements that go beyond the typical daily multivitamin.

Research has shown that most people do not get the required calcium and other daily micronutrients that are so important to building and maintaining strong bones and to preventing osteoporosis. Osteoporosis is a disease of bones that can lead to an increased risk of spinal compression fractures, loss of upright posture, hip fractures, pain and other skeletal problems. Osteoporosis is most common in women after menopause, when it is called postmenopausal osteoporosis, but may also develop in men, and may occur in anyone in the presence of particular hormonal disorders and other chronic diseases or as a result of medications, specifically glucocorticoids, when the disease is called steroid- or glucocorticoid-induced osteoporosis (SIOP or GIOP). Adequate calcium and vitamin D intake is an important part of preventing such bone problems for all men and woman over thirty years old.

Given its influence in the risk of fragility fracture, osteoporosis may significantly affect life expectancy and quality of life. Thus, there is a need for dietary supplements containing effective doses of vitamins, minerals, and antioxidants for providing nutritional support for bone health.

SUMMARY OF THE INVENTION

The present invention is based on the finding that certain vitamins, minerals, and antioxidants strengthen bones and/or joints, thereby inhibiting and/or ameliorating the symptoms associated with osteoporosis. In addition, such strengthening of the bones and/or joints is important for pre-operative and post-operative patients, and for general health and maintenance. Accordingly, in one aspect, the invention provides a dietary supplement formulation that includes vitamins, such as vitamin $D_3$, vitamin $K_1$, and vitamin $K_2$; and minerals, such as calcium and copper. In one embodiment, the vitamin $D_3$ present in an amount of about 2000 IU, the vitamin $K_1$ is present in an amount of about 100 mcg, the vitamin $K_2$ is present in an amount of about 20 mcg, the calcium is present in an amount of about 1000 mg, and the copper is present in an amount of about 1200 mcg.

In another aspect, the present invention also provides a dietary supplement formulation that includes vitamins, such as vitamin A, vitamin $B_1$, vitamin $B_2$, vitamin $B_3$, vitamin $B_5$, vitamin $B_6$, vitamin $B_{12}$, vitamin C, vitamin $D_3$, vitamin E, vitamin $K_1$, vitamin $K_2$, folate, biotin, and para-aminobenzoic acid (PABA); minerals, such as boron, calcium, chromium, copper, magnesium, manganese, molybdenum, potassium, selenium, vanadium, and zinc; and an antioxidant, such as pomegranate extract. In one embodiment, the vitamin A is present in an amount of about 5000 IU, the vitamin $B_1$ is present in an amount of about 50 mg, the vitamin $B_2$ is present in an amount of about 50 mg, the vitamin $B_3$ is present in an amount of about 25 mg, the vitamin $B_5$ is present in an amount of about 50 mg, the vitamin $B_6$ is present in an amount of about 100 mg, the vitamin $B_{12}$ is present in an amount of about 100 mcg, the vitamin C is present in an amount of about 400 mg, the vitamin $D_3$ is present in an amount of about 500 IU, the vitamin E is present in an amount of about 7.5 IU, the vitamin $K_1$ is present in an amount of about 500 mcg, the vitamin $K_2$ is present in an amount of about 5 mcg, the folate is present in an amount of about 400 mcg, the biotin is present in an amount of about 300 mcg, the PABA is present in an amount of about 30 mcg, the boron is present in an amount of about 1 mg, the calcium is present in an amount of about 50 mg, the chromium is present in an amount of about 200 mcg, the copper is present in an amount of about 450 mcg, the magnesium is present in an amount of about 150 mg, the manganese is present in an amount of about 15 mcg, the molybdenum is present in an amount of about 100 mcg, the potassium is present in an amount of about 100 mg, the selenium is present in an amount of about 60 mcg, the vanadium is present in an amount of about 50-100 mcg, the zinc is present in an amount of about 25 mg, and the pomegranate extract is present in an amount of about 1.2 mg.

In another aspect, the present invention provides a dietary supplement formulation that includes in combination all of the vitamins, minerals, and antioxidant from the above-described formulations. In one embodiment, the vitamin A is present in an amount of about 5000 IU, the vitamin $B_1$ is present in an amount of about 50 mg, the vitamin $B_2$ is present in an amount of about 50 mg, the vitamin $B_3$ is present in an amount of about 25 mg, the vitamin $B_5$ is present in an amount of about 50 mg, the vitamin $B_6$ is present in an amount of about 100 mg, the vitamin $B_{12}$ is present in an amount of about 100 mcg, the vitamin C is present in an amount of about 400 mg, the vitamin $D_3$ is present in an amount of about 2500 IU, the vitamin E is present in an amount of about 7.5 IU, the vitamin $K_1$ is present in an amount of about 600 mcg, the vitamin $K_2$ is present in an amount of about 25 mcg, the folate is present in an amount of about 400 mcg, the biotin is present in an amount of about 300 mcg, the PABA is present in an amount of about 30 mcg, the boron is present in an amount of about 1 mg, the calcium is present in an amount of about 1050 mg, the chromium is present in an amount of about 200 mcg, the copper is present in an amount of about 1650 mcg, the magnesium is present in an amount of about 150 mg, the manganese is present in an amount of about 15 mcg, the molybdenum is present in an amount of about 100 mcg, the potassium is present in an amount of about 100 mg, the selenium is present in an amount of about 60 mcg, the vanadium is present in an amount of about 50-100 mcg, the zinc is present in an amount of about 25 mg, and the pomegranate extract is present in an amount of about 1.2 mg.

In another aspect, the present invention is based on the finding that certain vitamins, minerals, and antioxidants strengthen bones or joints, thereby inhibiting and/or ameliorating the symptoms associated with bone diseases, such as osteoporosis. Accordingly, the present invention provides a method of treating a bone disease. Likewise, the invention provides a method of strengthening bones and/or joints. The method includes administering to a subject in need thereof a therapeutically effective amount of any of the dietary supplements provided herein. In one embodiment, the dietary supplement is administered to the subject daily. In another embodiment, the dietary supplement is administered to the subject once per day, twice per day, three times per day, four times per day, or more.

DETAILED DESCRIPTION OF THE INVENTION

The present invention is based on the finding that certain vitamins, minerals, and/or antioxidants enhance preparation for and/or recovery from bone and joint surgery.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the term "vitamin," refers to any of a group of organic substances essential in small quantities to normal metabolism in a subject. As such, the term "vitamin" includes, without limitation, thiamin, riboflavin, niacin, nicotinic acid, pantothenic acid, pyridoxine, biotin, folic acid, vitamin A, vitamin $B_1$, vitamin $B_2$, vitamin $B_3$, vitamin $B_5$, vitamin $B_6$, vitamin $B_{12}$, lipoic acid, ascorbic acid (vitamin C), vitamin D, vitamin $D_3$, vitamin E, vitamin $K_1$, vitamin $K_2$ and derivatives thereof. Also included within the term "vitamin" are the coenzymes thereof, as coenzymes are generally beneficial agents for the body. Coenzymes include thiamine pyrophosphates (TPP), flavin mononucleotides (FMM), flavin adenine dinucleotides (FAD), Nicotinamide adenine dinucleotides (AND), Nicotinamide adenine dinucleotide phosphate (NADP), Coenzyme-A (CoA) pyridoxal phosphate, biocytin, tetrahydrofolic acid, coenzyme $B_{12}$, lipoyllysine, 1,1-cis-retinal, and 1,2,5-dihydroxycholecalciferol. The term "vitamin" also includes choline, carnitine, and alpha, beta, and gamma carotenes. Thus, a vitamin may include, for example, substances that may or may not be required in the diet. Salts of vitamins are also suitable for use in the dietary supplement.

An effective amount of each vitamin contained in the dietary supplements of the invention is generally at least about 10% of the United States Recommended Daily Allowance ("RDA") for a patient. For example, an effective amount of vitamin C would include an amount of vitamin C sufficient to provide 10% or more of the RDA. However, it should be understood that the amount of each vitamin component may be less than 10% of the RDA, may exceed 100% of the RDA, or may be present regardless of whether the U.S. issued an RDA therefor.

As used herein, the term "mineral" refers to inorganic substances that are generally required in the diet. Thus, the term "mineral" includes, without limitation, calcium, iron, zinc, selenium, copper, iodine, magnesium, manganese, phosphorus, chromium, molybdenum, chloride, sodium, potassium, nickel, silicon, boron, vanadium, salts thereof, chelates, and other compositional forms and combinations thereof.

An effective amount of each mineral contained in the dietary supplement of the invention is generally at least about 10% of the United States Recommended Daily Allowance ("RDA") for a patient. For example, an effective amount of calcium would include an amount of calcium sufficient to provide 10% or more of the RDA. However, it should be understood that the amount of each mineral component may be less than 10% of the RDA, may exceed 100% of the RDA, or may be present regardless of whether the U.S. issued an RDA therefor.

As used herein, the term "antioxidant" refers to any of various substances that inhibit oxidation or reactions promoted by oxygen and peroxides and that include many held to protect the living body from the deleterious effects of free radicals. It should be understood that certain vitamins and/or minerals are known to be antioxidants, and while those components may be listed above, they are included within the term "antioxidant." Thus, the term "antioxidant" includes, without limitation, lutein, zeaxanthin, lycopene, and various extracts of fruits, such as pomegranate extract.

An effective amount of each antioxidant contained in the dietary supplements of the invention is generally at least about 10% of the United States Recommended Daily Allowance ("RDA") for a patient. For example, an effective amount of beta-carotene would include an amount of beta-carotene sufficient to provide 10% or more of the RDA. However, it should be understood that the amount of each antioxidant component may be less than 10% of the RDA, may exceed 100% of the RDA, or may be present regardless of whether the U.S. issued an RDA therefor.

Accordingly, in one aspect, the invention provides Dietary Supplement A, which includes one or more vitamins and one or more minerals. In one embodiment, the vitamins contained in Dietary Supplement A of the invention include vitamin $D_3$, vitamin $K_1$, and vitamin $K_2$. In another embodiment, the minerals contained in Dietary Supplement A of the invention include calcium and copper. Without being bound by theory calcium is known for critical support of nerve and muscle function, and optimized bone metabolism; vitamin $K_1$ is known for optimized clotting, bone mineralization, and cell growth; vitamin $K_2$ (as MK-4, menatetranone) has been shown in human clinical studies to lower risk of osteoporotic fractures by up to 81%; and copper citrate is known for energy production, connective tissue formation, iron metabolism, and cuproenzyme nervous system support. In addition, copper is required for optimized lysyl oxidase support of bone formation.

While it should be understood that the vitamins and minerals contained in Dietary Supplement A may be in any form known in the art, in one embodiment, the vitamin $D_3$ is present as cholecalciferol, the vitamin $K_1$ is present as phylloquinone, the vitamin $K_2$ is present as menatetranone (MK-4) and/or MK-6 and/or a mixture of MK-4 and MK-6, the calcium is present as calcium citrate, and the copper is present as copper citrate. In another embodiment, the calcium present in Dietary Supplement A is not in the form of calcium carbonate.

A typical serving of Dietary Supplement A will contain: vitamin $D_3$ present in an amount of about 1750 IU to about 2250 IU, vitamin $K_1$ present in an amount of about 75 mcg to about 150 mcg, vitamin $K_2$ present in an amount of about 10 mcg to about 30 mcg, calcium present in an amount of about 750 mg to about 1250 mg, and copper present in an amount of about 1000 mcg to about 1500 mcg. In one embodiment, a typical serving of Dietary Supplement A will contain: vitamin $D_3$ present in an amount of about 2000 IU, vitamin $K_1$ present in an amount of about 100 mcg, vitamin $K_2$ present in an amount of about 20 mcg, calcium present in an amount of about 1000 mg, and copper present in an amount of about 1200 mcg.

In another embodiment, Dietary Supplement A contains addition ingredients including, but are not limited to, stearic acid, croscarmellose sodium, modified cellulose and dicalcium phosphate, hydroxypropyl methylcellulose, magnesium stearate, silicon dioxide, brown rice, and water.

In yet another embodiment, Dietary Supplement A is specifically formulated to exclude various ingredients that are known in the art to be allergens. Exemplary ingredients, food products, or derivatives therefrom, that are specifically excluded from Dietary Supplement A are: casein or milk derivatives, corn, fish, shellfish, gluten, monosodium glutamate (MSG), nuts, processed sugar, soy, and wheat.

In another aspect, the invention provides Dietary Supplement B, which includes one or more vitamins, one or more minerals, and one or more antioxidants. In one embodiment, the vitamins contained in dietary supplement B of the invention include vitamin A, vitamin $B_1$, vitamin $B_2$, vitamin $B_3$, vitamin $B_5$, vitamin $B_6$, vitamin $B_{12}$, vitamin C, vitamin $D_3$, vitamin E, vitamin $K_1$, vitamin $K_2$, folate, biotin, and PABA (para-aminobenzoic acid or 4-aminobenzoic acid). In another embodiment, the minerals contained in Dietary Supplement B of the invention include boron, calcium, chromium, copper, magnesium, manganese, molybdenum, potassium, selenium, vanadium, and zinc. In yet another embodiment, the antioxidant contained in Dietary Supplement B of the invention includes pomegranate extract.

While it should be understood that the vitamins contained in Dietary Supplement B may be in any form known in the art, in one embodiment, the vitamin A is present as beta-carotene and/or retinyl acetate, the vitamin $B_1$ is present as thiamine HCl, the vitamin $B_2$ is present as riboflavin and/or riboflavin 5'-monophosphate, the vitamin $B_3$ is present as niacin, the vitamin $B_5$ is present as calcium D-pantothenate, the vitamin $B_6$ is present as pyridoxine HCl and/or pyridoxal 5'-phosphate, the vitamin $B_{12}$ is present as hydroxycobalamin, the vitamin C is present as L-ascorbate, the vitamin $D_3$ is present as cholecalciferol, the vitamin E is present as mixed tocopherols, the vitamin $K_1$ is present as phylloquinone, the vitamin $K_2$ is present as menatetranone (MK-4) and/or MK-6 and/or a mixture of MK-4 and MK-6, the folate is present as folic acid, and the biotin is present as scientifically pure crystalline biotin.

A typical serving of Dietary Supplement B will contain: vitamin A present in an amount of about 750 IU to about 7500 IU, vitamin $B_1$ present in an amount of about 20 mg to about 100 mg, vitamin $B_2$ present in an amount of about 5 mg to about 100 mg, vitamin $B_3$ present in an amount of about 10 mg to about 50 mg, vitamin $B_5$ present in an amount of about 25 mg to about 100 mg, vitamin $B_6$ present in an amount of about 20 mg to about 100 mg, vitamin $B_{12}$ present in an amount of about 50 mcg to about 150 mcg, vitamin C present in an amount of about 200 mg to about 500 mg, vitamin $D_3$ present in an amount of about 300 IU to about 600 IU, vitamin E present in an amount of about 5 IU to about 10 IU, vitamin $K_1$ present in an amount of about 300 mcg to about 600 mcg, vitamin $K_2$ present in an amount of about 2.5 mcg to about 7.5 mcg, folate present in an amount of about 300 mcg to about 500 mcg, biotin present in an amount of about 200 mcg to about 400 mcg, and PABA present in an amount of about 15 mcg to about 50 mcg. In one embodiment, the vitamin A is present in an amount of about 5000 IU (750 IU of retinyl acetate and 4250 IU of beta-carotene), the vitamin $B_1$ is present in an amount of about 50 mg, the vitamin $B_2$ is present in an amount of about 50 mg (45 mg riboflavin and 5 mg riboflavin 5'-monophosphate), the vitamin $B_3$ is present in an amount of about 25 mg, the vitamin $B_5$ is present in an amount of about 50 mg, the vitamin $B_6$ is present in an amount of about 100 mg (80 mg of pyridoxine HCl and 20 mg pyridoxal 5'-phosphate), the vitamin $B_{12}$ is present in an amount of about 100 mcg, the vitamin C is present in an amount of about 400 mg, the vitamin $D_3$ is present in an amount of about 500 IU, the vitamin E is present in an amount of about 7.5 IU, the vitamin $K_1$ is present in an amount of about 500 mcg, the vitamin $K_2$ is present in an amount of about 5 mcg, the folate is present in an amount of about 400 mcg, the biotin is present in an amount of about 300 mcg, and the PABA is present in an amount of about 30 mcg.

While it should be understood that the minerals contained in Dietary Supplement B may be in any form known in the art, in one embodiment, the boron is present as boron ascorbate, the calcium is present as calcium citrate, the chromium is present as chromium picolinate and/or chromium ascorbate, the copper is present as copper citrate, the magnesium is present as magnesium citrate and/or magnesium malate and/or magnesium succinate, the manganese is present as manganese ascorbate, the molybdenum is present as molybdenum ascorbate, the potassium is present as potassium citrate, the selenium is present as L-selenomethianone, the vanadium is present as vanadium ascorbate, and the zinc is present as zinc picolinate. In another embodiment, the calcium present in Dietary Supplement B is not in the form of calcium carbonate.

A typical serving of Dietary Supplement B will contain: boron present in an amount of about 0.5 mg to about 2 mg, calcium present in an amount of about 25 mg to about 75 mg, chromium present in an amount of about 100 mcg to about 300 mcg, copper present in an amount of about 250 mcg to about 550 mcg, magnesium present in an amount of about 100 mg to about 200 mg, manganese present in an amount of about 10 mcg to about 30 mcg, molybdenum present in an amount of about 50 mcg to about 200 mcg, potassium present in an amount of about 50 mg to about 150 mg, selenium present in an amount of about 30 mcg to about 90 mcg, about 50 mcg to 100 mcg vanadium, and zinc present in an amount of about 10 mg to about 50 mg. In another embodiment, the boron is present in an amount of about 1 mg, the calcium is present in an amount of about 50 mg, the chromium is present in an amount of about 200 mcg (100 mcg of chromium picolinate and 100 mcg of chromium ascorbate), the copper is present in an amount of about 450 mcg, the magnesium is present in an amount of about 150 mg, the manganese is present in an amount of about 15 mcg, the molybdenum is present in an amount of about 100 mcg, the potassium is present in an amount of about 100 mg, the selenium is present in an amount of about 60 mcg, the vanadium is present in an amount of about 50-100 mcg, and the zinc is present in an amount of about 25 mg.

While it should be understood that the antioxidants contained in Dietary Supplement B may be in any form known in the art, in one embodiment, the antioxidant is pomegranate extract. In another embodiment, the pomegranate extract is present in an amount of about 0.5 mg to about 5 mg. In yet another embodiment, the pomegranate extract is present in an amount of about 1.2 mg.

In another embodiment, Dietary Supplement B contains addition ingredients including, but are not limited to, stearic acid, croscarmellose sodium, modified cellulose and dicalcium phosphate, magnesium stearate, silicon dioxide, and microcrystalline cellulose.

In yet another embodiment, Dietary Supplement B is specifically formulated to exclude various ingredients that are known in the art to be allergens. Exemplary ingredients, food products, or derivatives therefrom, that are specifically excluded from Dietary Supplement B are: casein or milk derivatives, corn, fish, shellfish, gluten, monosodium glutamate (MSG), nuts, processed sugar, soy, and wheat.

In yet another embodiment, the formulations of Dietary Supplement A and Dietary Supplement B omit or minimize the amounts of vitamin E (or other tocopherols) and herbal medicines in order to reduce or prevent the known potential for drug or anesthetic reaction during surgery. For example, most vitamin E forms are known to strongly and unpredictably potentiate the effects of general anesthesia and other peri-operative agents, raising surgical and perioperative risks, and are therefore not recommended.

In another aspect, the invention provides Dietary Supplement C, which includes the above-discussed ingredients of Dietary Supplement A and Dietary Supplement B. In one embodiment, the ingredients of Dietary Supplement A and Dietary Supplement B are formulated separately (e.g., as separate tablets) for individualized administration to a subject in need of dietary supplementation. In another embodiment, the ingredients of Dietary Supplement A and Dietary Supplement B are formulated into a single unit for simultaneous administration to the subject. It should be understood that, regardless of how Dietary Supplement C is formulated, Dietary Supplement C is intended to contain the total amounts of each ingredient of Dietary Supplement A and Dietary Supplement B, as disclosed above. In one embodiment, Dietary Supplement C contains more than 100% RDA of calcium.

As such, typical serving of Dietary Supplement C will contain: about 750 IU to 7500 IU of vitamin A, about 20 mg to 100 mg of vitamin $B_1$, about 5 mg to 100 mg of vitamin $B_2$, about 10 mg to 50 mg of vitamin $B_3$, about 25 mg to 100 mg of vitamin $B_5$, about 20 mg to 100 mg of vitamin $B_6$, about 50 mcg to 150 mcg of vitamin $B_{12}$, about 200 mcg to 500 mg of vitamin C, about 1750 IU to 2250 IU of vitamin $D_3$, about 5 IU to 10 IU of vitamin E, about 300 mcg to 600 mcg of vitamin $K_1$, about 10 mcg to 30 mcg of vitamin $K_2$, about 300 mcg to 500 mcg of folate, about 200 mcg to 400 mcg of biotin, about 15 mcg to 50 mcg PABA, about 0.5 mg to 2 mg boron, about 750 mg to 1250 mg calcium, about 100 mcg to 300 mcg chromium, about 1000 mcg to 1500 mcg mcg copper, about 100 mg to 200 mg magnesium, about 10 mcg to 30 mcg manganese, about 50 mcg to 200 mcg molybdenum, about 50 mg to 150 mg potassium, about 30 mcg to 90 mcg selenium, about 50 mcg to 100 mcg vanadium, about 10 mg to 50 mg zinc, and about 0.5 mg to 5 mg pomegranate extract. In one embodiment, the vitamin A is present in an amount of about 5000 IU, the vitamin $B_1$ is present in an amount of about 50 mg, the vitamin $B_2$ is present in an amount of about 50 mg, the vitamin $B_3$ is present in an amount of about 25 mg, the vitamin $B_5$ is present in an amount of about 50 mg, the vitamin $B_6$ is present in an amount of about 100 mg, the vitamin $B_{12}$ is present in an amount of about 100 mcg, the vitamin C is present in an amount of about 400 mg, the vitamin $D_3$ is present in an amount of about 2500 IU, the vitamin E is present in an amount of about 7.5 IU, the vitamin $K_1$ is present in an amount of about 600 mcg, the vitamin $K_2$ is present in an amount of about 25 mcg, the folate is present in an amount of about 400 mcg, the biotin is present in an amount of about 300 mcg, the PABA is present in an amount of about 30 mcg, the boron is present in an amount of about 1 mg, the calcium is present in an amount of about 1050 mg, the chromium is present in an amount of about 200 mcg, the copper is present in an amount of about 1650 mcg, the magnesium is present in an amount of about 150 mg, the manganese is present in an amount of about 15 mcg, the molybdenum is present in an amount of about 100 mcg, the potassium is present in an amount of about 100 mg, the selenium is present in an amount of about 60 mcg, the vanadium is present in an amount of about 50-100 mcg, the zinc is present in an amount of about 25 mg, and the pomegranate extract is present in an amount of about 1.2 mg. In another embodiment, the vitamin A is present as about 750 IU of retinyl acetate and about 4250 IU of beta-carotene, the vitamin $B_2$ is present as about 45 mg of riboflavin and about 5 mg of riboflavin 5'-monophosphate, and the vitamin $B_6$ is present as about 80 mg of pyridoxine HCl and about 20 mg of pyridoxal 5'-phosphate.

Any of the dietary supplement formulations of the invention may further include one or more additional adjuvants, which can be chosen from those known in the art, provided that the adjuvants are not specifically excluded as detailed above. For example, adjuvants including flavors, sweeteners, colors, binders, diluents, filler, compaction agents, non-effervescent disintegrants, and the like, commonly referred to as excipients, may be included.

Suitable flavors for use in the dietary supplement formulation may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the organoleptic effect desired. Flavors may be present in an amount ranging from about 0.5% to about 3.0% by weight of the composition. Commonly accepted flavors include grape and cherry flavors, and citrus flavors such as orange. It is also appreciated that inclusion of flavoring agents can influence the final flavor of the vehicle, furthering compliance with ingestion of the dietary supplement.

Suitable sweeteners for use in the composition of the invention include, but are not limited to, carbohydrates, mono-saccharides, di-saccharides, polysaccharides of simple sugars, and sugar derivatives. Exemplary sweeteners include, but are not limited to, high caloric sugars such as sucrose, lactose, glucose, d-glucose, l-glucose, maltose, dextrose, fructose, fructosan, gentiobiose, cellobiose, panose, maltotriose, malto-tetrose, arabinose, mannose, d-mannose, galactose, d-galactose, d-glyceraldehyde, amylose, allose, altose, talose, gulose, idose, ribose, erythrose, threose, lyxose, xylose, d-xylose, rhamnose, invert sugar, inositol, glycerol, glycogen, pectin, agar, sorbitol, mannitol and combinations thereof; low caloric sugars, such as sucralose, polyols, tagarose, trehalose, xylitol, dextrans, dextrins, dextrates, polysorbates, maltodextrin, xylitol, amylase, amylopectin, ribose, β-maltose, fucose, sialic acid (neuraminic acid), N-acetylgalactosamine, N-acetylglucosamine, sedoheptulose, ribulose, xylulose and combinations thereof; non-sugar sweeteners, such as acesulfane potassium, aspartame, neotame, saccharin, stevioside and combinations thereof.

Coloring agents may include titanium dioxide, and dyes suitable for food such as those known as F. D. & C. dyes and natural coloring agents such as grape skin extract, beet red powder, beta-carotene, annato, carmine, turmeric, paprika, etc. The amount of coloring used may range from about 0.1% to about 3.5% by weight of the final composition.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount up to about 60% by weight and advantageously from about 10% to about 40% by weight of the total composition.

Other disintegrants that may be used in the dietary supplements of the invention include, but are not limited to, starches as potato starch and modified starches thereof, sweeteners, clays, such as bentonite, micro-crystalline cellulose, alginates, gums such as agar, guar, locust bean, karaya, pecitin and tragacanth. Disintegrants may comprise up to about 20% by weight and advantageously between about 2% and about 10% by weight of the final composition. Notably, these binders and disintegrants may already be sufficiently present in other components of the formulation.

The individual components of the dietary supplements of the invention are formulated into a solid composition for oral administration to a subject in need of dietary supplementation. Suitable solid compositions include, without limitation, orally dispersable pills, chewable pills, buccal adhesive pills, tablets, capsules including hard or soft-shelled gelatin capsules, granular powder, troches, and dragees. These formulations may be prepared by techniques known in the art. For example, a pill may be manufactured by well-known pill manufacturing procedures.

Known granulation and wet-granulation methods for forming tablets may be utilized. Granulation generally includes any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation. Granulation also includes, for example, a process where a liquid form of a material is rendered granular, or in a solid form, by combining it with a granular core material, such as a sugar particle. Such granular material may be produced, for example, by spray-drying the liquid onto the core particle. Thus, individual materials may be granulated to lend themselves to tableting.

Lubricants are normally used in the manufacture of tablets. Without the use of an effective lubricant, tableting by use of high-speed equipment may be difficult. As used herein, the term "lubricant" refers to a material that can reduce the friction arising at the interface of the tablet and the die wall during compression and ejection thereof. Lubricants may also serve to prevent sticking to the punch and, to a lesser extent, the die wall as well.

Extrinsic or intrinsic lubricants may be incorporated in the material to be tableted. A lubricant that is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity. Magnesium, calcium and zinc salts of stearic acid have long been regarded as the most efficient intrinsic lubricants in common use. Concentrations of 1% or less by weight are usually effective.

Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, magnesium oxide and the like. See Leal, et al., U.S. Pat. No. 3,042,531, the disclosure of which is incorporated herein by reference in its entirety.

In another aspect, the dietary supplements of the invention may be formulated into a solid composition for placement in an aqueous vehicle for oral administration. In this embodiment, it is contemplated that the formulation would further include an effervescing agent for dispersing the components of the formulation within the aqueous vehicle. As used herein, the term "aqueous vehicle" refers to a medium or a carrier, such as a foodstuff, containing at least a minimal amount of water. Thus, the aqueous vehicle may be an oligohydrous vehicle containing a small amount of water, or it may be a vehicle having an abundance of water contained therein.

The term "foodstuff," as used herein, is intended to refer to any safe, consumable liquid, semi-solid, or solid substance. Thus, a foodstuff would include any beverage and any food, which may be consumed by mammals of all classes and ages. As used herein, the term "effervescence" generally means the escape of a gas from a liquid or mixture (Hawley's Chemical Dictionary, pp. 432, 2001). Thus, the term "effervescent agent," is intended to generally refer to a composition or mixture of components that evolve one or more gases, under proper conditions, such as upon contact with water.

In one embodiment, the effervescing agent is a mixture of compounds that evolve gas. These compounds should be capable of reacting upon exposure of one or both of the reactants to water, such as the water contained in aqueous fluids or other aqueous vehicles, to produce and/or evolve the gas. In one embodiment, the effervescing mixture includes at least one acidic component and at least one basic component. In this instance, the acidic and basic components react, upon exposure to water, with one another to produce at least one gas. For example, the reaction between a soluble acid, or source thereof, with an carbonate, or source thereof such as an alkaline metal carbonate, generally evolves $CO_2$ gas. More particularly, when such a gas-generating effervescent mixture is placed in a minimal amount of water, or water-containing vehicle such as saliva, $CO_2$ gas is generally produced and bubbles out of the water or aqueous vehicle.

The acidic component may be an acid or source thereof and should be safe for consumption. Suitable acids include, but are not limited to, food acids, acid anhydrides and acid salts. Exemplary food acids include, but are not limited to, citric acid, tartaric acid, malic acid, fumaric acid, adipic acid, and succinic acid. Anhydrides of the above-described acids may also be used because anhydrides generally degrade in the presence of water to generate the reactive acid. Exemplary suitable acid salts include, but are not limited to, sodium dihydrogen phosphate, disodium dihydrogen pyrophosphate, acid citrate salts and sodium acid sulfite. Acid salts generally disassociate in water, or in the water content of the aqueous vehicle, to provide the reactive acid species. The overall solubility of the acid, or source thereof, in water will vary and is appreciated by those of skill in the art. The effectiveness of the acid in generating the gas, and the amount of gas generated, is generally dependent on water solubility of the acid form in the dietary supplement.

Similarly, the basic component may be a carbonate or source thereof and should be safe for consumption. Suitable carbonate sources include, but are not limited to, dry solid carbonate, bicarbonate, sesquicarbonate, and sesquibicarbonate salts of metals, such as sodium, potassium, lithium, calcium, and magnesium. Examples of suitable carbonates include, without limitation, sodium carbonate, sodium bicarbonate, sodium sesquicarbonate, potassium carbonate, potassium bicarbonate, potassium sesquicarbonate, magnesium carbonate, sodium glycine carbonate, L-lysine carbonate, arginine carbonate, and amorphous calcium carbonate. Ammonium carbonate and ammonium bicarbonate are also suitable carbonates. In addition, any combination of the above sources of carbonate may be used as the basic component in the effervescing mixture.

It should be understood that the gas-generating effervescent component(s) are not limited to components reactive to form only carbon dioxide gas. Pharmaceutically safe reactants that evolve oxygen, nitrogen, helium, ethylene oxide, or other inert gases are also considered within the scope of the invention. For example, peroxides such as hydrogen peroxide, sodium peroxide and the like are capable of releasing useful oxygen gas. The combination of horse-radish with hydrogen peroxidase for example, or a vegetable peroxidase, is known to evolve oxygen gas. In addition, the gas-generating effervescent component(s) are not limited to mutually reactive components, such as the acidic and basic components described above, but may include safe, compounds, reactive with water to release a gas. Use of safe gas-generating effervescent component(s) and gases generated therefrom is particularly important in dietary supplements designed for oral administration.

The effectiveness of the effervescing agent to disperse the vitamins, minerals, and antioxidants of the dietary supplement is generally related to the degree of "pop" caused by the abrupt release of gas. As disclosed in U.S. Pat. No. 4,837,039, the disclosure of which is incorporated herein by reference in its entirety, the quantity and intensity of each "pop" is generally dependent upon the size of the bubble, the pressure of the gas contained in the bubble, the surface tension of the bubble, and the degree of solubility of the ingredients of the solid matrices in water or an aqueous vehicle. For example, the intensity of the release of gas depends upon the relation of the pressure of the occluded gas to resistance of the film of the bubble and on the diameter of the bubble trapping the gas.

In one embodiment, the dietary supplements of the invention may be formulated to optimize exposure of the effervescing agent to the water content of the aqueous vehicle. For example, the formulation may contain a plurality of layers including an outermost layer and a core. Any of the components, including the effervescing agents, vitamins, minerals, and antioxidants, may be included in the outermost layer or distributed as desired between the outermost layer and the core. Thus, bi-layered or multi-layered tablet or pill formulations are contemplated herein.

In yet another embodiment, the dietary supplement is varied in shape. For example, while conventional oval shapes of a tablet or round shapes of a pill exist, the formulation may be provided in a non-traditional shape so as to increase the surface area of the formulation that is exposed to the vehicle. Particularly, for oligohydrous vehicles having minimal water content, exposing a maximum surface area of the formulation will enhance the rate of effervescence, thereby promoting the rate of distribution of the vitamins, minerals, and antioxidants into the vehicle. Generally, patients do not prefer to wait for a lengthy period of time before ingesting the vehicle. Therefore, in one embodiment of the invention, the solid formulation, such as a tablet or pill, has a biconcave shape to increase the surface area for contact with the vehicle. Such a shape may also comprise multiple layers, as previously discussed herein, wherein one or more layers contain one or more of the components of the dietary supplement. Optimal exposure of these components generally minimizes the time required to disperse the vitamins, minerals, and antioxidants into the vehicle by the effervescence of gas.

Formulations containing an effervescing agent may be orally administered to the subject in need of dietary supplementation in a variety of ways. For example, the tablet(s) is initially placed in an aqueous vehicle, where it may be further stirred and/or agitated to commence effervescence of gases within the vehicle. Vehicles containing as little as about 0.1 ml of total water content are generally suitable to commence effervescence of gas(es) from the formulation. The effervescing gases promote penetration and distribution of the vitamins, minerals, and antioxidants into the vehicle. In one embodiment, the dietary supplement formulation is placed into a vehicle containing up to about 5 ml of water. In another embodiment, the dietary supplement formulation is placed into a vehicle containing up to about 6 ounces of water. In another embodiment, the effervescent formulation is placed in a vehicle containing between about 5 ml and about 15 ml of water. In yet another embodiment, the effervescent formulation is placed in a vehicle containing at least about 15 ml of water.

In another aspect, the invention provides a method for ameliorating/treating bone diseases associated with a vitamin, mineral, and/or antioxidant deficiency in a subject. Likewise, the invention provides methods for strengthening bones and/or joints, either pre-operative, post-operative, or for general health and maintenance. The methods include administering to a subject tin need thereof a therapeutically effective amount of Dietary Supplement A, Dietary Supplement B, or Dietary Supplement C. It should be understood that Dietary Supplement C consists of Dietary Supplement A and Dietary Supplement B, as discussed above.

As used herein, the term "ameliorating" or "treating" means that the clinical signs and/or the symptoms associated with a boner disorder (e.g., osteoporosis) are lessened as a result of the actions performed. The signs or symptoms to be monitored will be characteristic of osteoporosis and will be well known to the skilled clinician, as will the methods for monitoring the signs and conditions. Also included in the definition of "ameliorating" or "treating" is the lessening of symptoms associated with such disorders in subjects not yet diagnosed as having the specific disorders. As such, the methods may be used as a means for prophylactic therapy for a subject at risk of having a specific bone disorder (e.g., osteoporosis).

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of the term "subject."

In one embodiment, the dietary supplement formulations of the inventions are administered to a subject that is pre-operative or post-operative to aid in preparation for surgery and/or healing and recovery therefrom. Thus, the dietary supplement formulations address the micronutrient (vitamin/mineral/co-factor) needs for preparation and healing from the specific unique tissue demands of bone and joint surgery (e.g., shoulder surgery, elbow surgery, hand surgery, hip surgery, knee surgery, ankle surgery, spine surgery, and fracture surgery, etc). The dietary supplement formulations may further be combined with other vitamins/minerals/co-factors to provide targeted supplement combinations specific for a wide array of other surgery types (e.g., cardiac surgery, urology surgery, gynecologic surgery, ocular surgery, plastic surgery and bariatric surgery).

In another embodiment, the dietary supplement formulations of the inventions are administered to a subject to strengthen bones and/or joints for general health and maintenance.

As used herein, the term "therapeutically effective amount" or "effective amount" means the amount of a compound or pharmaceutical composition that will elicit the biological or medical response of a tissue, system, animal or human that is being sought by the researcher, veterinarian, medical doctor or other clinician. The terms "administration" or "administering" are defined to include the act of providing a compound or pharmaceutical composition of the invention to a subject in need of treatment. While the dietary supplements of the invention are disclosed for oral administration, it should be understood that the compositions may be administered by any means determined by the researcher, veterinarian, medical doctor or other clinician for treating the subject. Exemplary modes of administration include, but are not limited to, intravenously, intra-arterially, subcutaneously, intraperitoneally, intramuscularly, or orally. Thus, in one embodiment, the dietary supplements are orally ingested.

The total amount of the dietary supplements to be administered in practicing a method of the invention can be administered to a subject as a single dose or can be administered using a fractionated treatment protocol, in which multiple doses are administered over a prolonged period of time (e.g., once daily, twice daily, etc.). When administered orally in pill or tablet form, a dose or serving size of the dietary supplements of the invention may be administered as a single tablet or fractionated into multiple (e.g., 2, 3, 4, 5, 6, or more) tablets. As such, in one embodiment, the dietary supplement is administered to the subject daily. In another embodiment, the dietary supplement is administered to the subject once per day, twice per day, three times per day, four times per day, or more often.

In certain embodiments, the dietary supplements of the invention may further be administered in combination with other vitamin/mineral/antioxidant formulations. In yet other embodiments, the dietary supplements of the invention may further be administered in combination with an antiinflammatory, antimicrobial, antihistamine, chemotherapeutic agent, antiangiogenic agent, immunomodulator, therapeutic antibody or a protein kinase inhibitor, e.g., a tyrosine kinase inhibitor, to a subject in need of such treatment. Other agents that may be administered in combination with invention compounds include protein therapeutic agents such as cytokines, immunomodulatory agents and antibodies. While not wanting to be limiting, antimicrobial agents include antivirals, antibiotics, anti-fungals and anti-parasitics. When other therapeutic agents are contemplated for use in combination with the dietary supplement of the present invention, they may be used for example in amounts as noted in the Physician Desk Reference (PDR) or as otherwise determined by one having ordinary skill in the art.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Dietary Supplement A Formulation

The formulation was produced such that a full dose/serving is contained in four tablets. Each dose/serving of the dietary supplement contains the following:
- calcium (as calcium carbonate): 1000 mg
- vitamin D (as vitamin D3, cholecalciferol): 2000 IU
- vitamin $K_1$ (phylloquinone): 100 mcg
- vitamin $K_2$ (menatetranone, MK-4): 20 mcg
- copper (copper citrate): 1200 mcg
- Other ingredients: stearic acid, croscarmellose sodium, modified cellulose and dicalcium phosphate, hydroxypropyl methylcellulose, magnesium stearate, silicon dioxide, brown rice, and water.
- Formulated to Exclude: casein or milk derivatives, corn, fish or shellfish, gluten, MSG, nuts, processed sugar, soy, and wheat.

EXAMPLE 2

Dietary Supplement B Formulation

The formulation was produced such that a full dose/serving is contained in two tablets. Each dose/serving of the dietary supplement contains the following:
- vitamin A (beta-carotene): 5000 IU
  - 15% retinyl acetate: 750 IU
  - 85% beta-carotene: 4250 IU
- vitamin $B_1$ (Thiamine HCl): 50 mg
- vitamin $B_2$: 50 mg
  - riboflavin: 45 mg
  - riboflavin 5'-monophosphate: 5 mg
- vitamin $B_3$ (niacin): 25 mg
- vitamin $B_5$ (calcium D-pantothenate): 50 mg
- vitamin $B_6$: 100 mg
  - pyridoxine HCl: 80 mg
  - pyridoxal 5'-phosphate: 20 mg
- vitamin $B_{12}$ (hydroxycobalamin): 100 mcg
- vitamin C (L-ascrobate): 400 mg
- vitamin $D_3$ (cholecalciferol): 500 IU
- vitamin E (as mixed tocopherols): 7.5 IU
- vitamin $K_1$ (phylloquinone): 500 mcg
- vitamin $K_2$ (menatetranone, MK-4): 5 mcg
- biotin (crystalline-scientifically pure): 300 mcg
- folate (folic acid): 400 mcg
- PABA: 30 mcg
- boron (boron ascorbate): 1 mg
- calcium (calcium citrate): 50 mg
- chromium: 200 mcg
  - chromium picolinate: 100 mcg
  - chromium ascorbate: 100 mcg
- copper (copper citrate): 450 mcg
- magnesium (as magnesium citrate, magnesium malate, magnesium succinate): 150 mg
- manganese (manganese ascorbate): 15 mcg
- molybdenum (molybdenum ascorbate): 100 mcg
- potassium (potassium citrate): 100 mg
- selenium (L-selenomethianone): 60 mcg
- vanadium (vanadium ascorbate): 50-100 mcg (prefer not to exceed 100 mcg)
- zinc (zinc picolinate): 25 mg pomegranate extract (Antioxidant): 1.2 mg
Other ingredients: dicalcium phosphate, microcrystalline cellulose, croscarmellose sodium, stearic acid, modified cellulose, magnesium stearate, and silicon dioxide.
Formulated to Exclude: casein or milk derivatives, corn, fish or shellfish, gluten, MSG, nuts, processed sugar, soy, and wheat.

EXAMPLE 3

Combination of Dietary Supplements A and B

Serving size is four tablets of Dietary Supplement A Formulation and two tablets of Dietary Supplement B Formulation. As such, a subject consumes the total amount of Dietary Supplements A and B.

Although the invention has been described with reference to the above example, it will be understood that modifications and variations are encompassed within the spirit and scope of the invention. Accordingly, the invention is limited only by the following claims.

What is claimed is:

1. A dietary supplement consisting of:
calcium (as calcium carbonate): 1000 mg,
vitamin D (as vitamin D3, cholecalciferol): 2000 IU,
vitamin $K_1$ (phylloquinone): 100 mcg,
vitamin $K_2$ (menatetranone, MK-4): 20 mcg,
copper (copper citrate): 1200 mcg,
stearic acid, croscarmellose sodium, modified cellulose, dicalcium phosphate, hydroxypropyl methylcellulose, magnesium stearate, silicon dioxide, brown rice and water.

2. A dietary supplement comprising:
vitamin A (beta-carotene): 5000 IU,
15% retinyl acetate: 750 IU,
85% beta-carotene: 4250 IU,
vitamin $B_1$ (Thiamine HCl): 50 mg,
vitamin $B_2$: 50 mg,
riboflavin: 45 mg,
riboflavin 5'-monophosphate: 5 mg,
vitamin $B_3$ (niacin): 25 mg,
vitamin $B_5$ (calcium D-pantothenate): 50 mg,
vitamin $B_6$: 100 mg,
pyridoxine HCl: 80 mg,
pyridoxal 5'-phsophate: 20 mg,
vitamin $B_{12}$ (hydroxycobalamin): 100 mcg,
vitamin C (L-ascorbate): 400 mg,
vitamin $D_3$ (cholecalciferol): 500 IU,
vitamin E (as mixed tocopherols): 7.5 IU,
vitamin $K_1$ (phylloquinone): 500 mcg,
vitamin $K_2$ (menatetranone, MK-4): 5 mcg,
biotin (crystalline-scientifically pure): 300 mcg,
folate (folic acid): 400 mcg,
PABA: 30 mcg,
boron (boron ascorbate): 1 mg,
calcium (calcium citrate): 50 mg,
chromium: 200 mcg,
chromium picolinate: 100 mcg,
chromium ascorbate: 100 mcg,
copper (copper citrate): 450 mcg,
magnesium (as magnesium citrate, magnesium malate or magnesium succinate): 150 mg,
manganese (manganese ascorbate): 15 mcg,
molybdenum (molybdenum ascorbate): 100 mcg,
potassium (potassium citrate): 100 mg,
selenium (L-selenomethianone): 60 mcg,
vanadium (vanadium ascorbate): 50-100 mcg,
zinc (zinc picolinate): 25 mg,
pomegranate extract: 1.2 mg,
dicalcium phosphate, microcrystalline cellulose, croscarmellose sodium, stearic acid, modified cellulose, magnesium stearate and silicon dioxide.

3. A combination dietary supplement comprising:
a first dietary supplement comprising:
calcium (as calcium carbonate): 1000 mg,
vitamin D (as vitamin D3, cholecalciferol): 2000 IU,
vitamin $K_1$ (phylloquinone): 100 mcg,
vitamin $K_2$ (menatetranone, MK-4): 20 mcg,
copper (copper citrate): 1200 mcg,
stearic acid, croscarmellose sodium, modified cellulose, dicalcium phosphate, hydroxypropyl methylcellulose, magnesium stearate, silicon dioxide, brown rice, and water and
a second dietary supplement comprising:
vitamin A (beta-carotene): 5000 IU,
15% retinyl acetate: 750 IU,
85% beta-carotene: 4250 IU,
vitamin $B_1$ (Thiamine HCl): 50 mg,
vitamin $B_2$: 50 mg,
riboflavin: 45 mg,
riboflavin 5'-monophosphate: 5 mg,
vitamin $B_3$ (niacin): 25 mg,
vitamin $B_5$ (calcium D-pantothenate): 50 mg,
vitamin $B_6$: 100 mg,
pyridoxine HCl: 80 mg,
pyridoxal 5'-phsophate: 20 mg,
vitamin $B_{12}$ (hydroxycobalamin): 100 mcg,
vitamin C (L-ascorbate): 400 mg,
vitamin $D_3$ (cholecalciferol): 500 IU,
vitamin E (as mixed tocopherols): 7.5 IU,
vitamin $K_1$ (phylloquinone): 500 mcg,
vitamin $K_2$ (menatetranone, MK-4): 5 mcg,
biotin (crystalline-scientifically pure): 300 mcg,
folate (folic acid): 400 mcg,
PABA: 30 mcg,
boron (boron ascorbate): 1 mg,
calcium (calcium citrate): 50 mg,
chromium: 200 mcg,
chromium picolinate: 100 mcg,
chromium ascorbate: 100 mcg,
copper (copper citrate): 450 mcg,
magnesium (as magnesium citrate, magnesium malate or magnesium succinate): 150 mg,
manganese (manganese ascorbate): 15 mcg,
molybdenum (molybdenum ascorbate): 100 mcg,
potassium (potassium citrate): 100 mg,
selenium (L-selenomethianone): 60 mcg,
vanadium (vanadium ascorbate): 50-100 mcg,
zinc (zinc picolinate): 25 mg,
pomegranate extract: 1.2 mg,
dicalcium phosphate, microcrystalline cellulose, croscarmellose sodium, stearic acid, modified cellulose, magnesium stearate and silicon dioxide.

* * * * *